United States Patent
Warren et al.

(10) Patent No.: US 10,436,732 B2
(45) Date of Patent: Oct. 8, 2019

(54) NEAR FULL HOOP ELECTRICAL AXIAL SHIFT WEAR INDICATION SENSOR

(71) Applicant: United Technologies Corporation, Farmington, CT (US)

(72) Inventors: Eli Cole Warren, Wethersfield, CT (US); Peter J. Walsh, Wethersfield, CT (US)

(73) Assignee: United Technologies Corporation, Farmington, CT (US)

( * ) Notice: Subject to any disclaimer, the term of this patent is extended or adjusted under 35 U.S.C. 154(b) by 111 days.

(21) Appl. No.: 15/696,929

(22) Filed: Sep. 6, 2017

(65) Prior Publication Data

US 2019/0072511 A1 Mar. 7, 2019

(51) Int. Cl.
*G01N 27/20* (2006.01)
*F01D 21/00* (2006.01)
*F01D 5/12* (2006.01)
*G01M 15/14* (2006.01)
*G01B 7/14* (2006.01)

(52) U.S. Cl.
CPC .............. *G01N 27/20* (2013.01); *F01D 5/12* (2013.01); *F01D 21/003* (2013.01); *G01B 7/14* (2013.01); *G01M 15/14* (2013.01); *F05D 2220/32* (2013.01); *F05D 2260/83* (2013.01)

(58) Field of Classification Search
CPC ......... G01N 27/20; F01D 21/003; F01D 5/12; F05D 2260/83; F05D 2220/32
See application file for complete search history.

(56) References Cited

U.S. PATENT DOCUMENTS

| | | | |
|---|---|---|---|
| 6,717,420 | B2 | 4/2004 | Eyraud et al. |
| 7,511,516 | B2 | 3/2009 | Nigmatulin et al. |
| 8,151,623 | B2 | 4/2012 | Shinde et al. |
| 2005/0158511 | A1 | 7/2005 | Sabol et al. |

(Continued)

FOREIGN PATENT DOCUMENTS

WO 2005083411 A1 9/2005

OTHER PUBLICATIONS

Four-terminal sensing, available Mar. 17, 2017 at https://en.wikipedia.org/wiki/Four-terminal_sensing (Four-terminal sensing (Year: 2017).*

(Continued)

*Primary Examiner* — Daniel R Miller
(74) *Attorney, Agent, or Firm* — Cantor Colburn LLP (57) ABSTRACT

A wear indication sensor comprising: a resistor strip configured to be operably attached to the surface of an engine component, the resistor strip including a first end and second end; a plurality of lead wires comprising: a first lead wire electrically connected to the first end proximate an aft end of the engine component; a second lead wire electrically connected to the first end proximate a forward end of the engine component; a third lead wire electrically connected to the second end proximate the aft end of the engine component; and a fourth lead wire electrically connected to the second end proximate the forward end of the engine component; and a measurement device electrically connected to each of the plurality of lead wires, wherein the measurement device is configured to measure a resistance of the resistor strip between each of the plurality of lead wires.

19 Claims, 8 Drawing Sheets

(56) References Cited

U.S. PATENT DOCUMENTS

2009/0243585 A1* 10/2009 Andarawis ........... G01N 27/041
                                                    324/71.2
2010/0242293 A1    9/2010 Willett et al.

OTHER PUBLICATIONS

Extended European Search Report for Application No. 18192991.0-1001; Report dated Feb. 4, 2019; Report Received Date: Feb. 13, 2019.

* cited by examiner

NEAR FULL HOOP ELECTRICAL AXIAL SHIFT WEAR INDICATION SENSOR

BACKGROUND

The subject matter disclosed herein generally relates to measurement devices and, more particularly, to a method and an apparatus for detecting blade tip clearance and axial shift for a gas turbine engine.

Gas turbine engines typically include a compressor, a combustor, and a turbine, with an annular flow path extending axially through each. Initially, air flows through the compressor where it is compressed or pressurized. The combustor then mixes and ignites the compressed air with fuel, generating hot combustion gases. These hot combustion gases are then directed from the combustor to the turbine where power is extracted from the hot gases by causing blades of the turbine to rotate.

The compressor and turbine sections include multiple rotors and stators configured to enable optimal operation. Gas turbine engines maintain an optimal clearance (distance) between the tips of the rotor blade and an outside diameter of a gas path within the turbine engine, and thereby provide the conditions necessary to achieve a desired performance. The blade tips may cut into the outer diameter when the blade tips extend radially outward. The radial depth of cut and the axial length of the cut may both affect the efficiency of the gas turbine engine.

SUMMARY

According to one embodiment, a wear indication sensor is provided. The wear indication sensor comprising: a resistor strip configured to be operably attached to the surface of an engine component, the resistor strip including a first end and a second end; a plurality of lead wires comprising: a first lead wire electrically connected to the first end of the resistor strip proximate an aft end of the engine component; a second lead wire electrically connected to the first end of the resistor strip proximate a forward end of the engine component; a third lead wire electrically connected to the second end of the resistor strip proximate the aft end of the engine component; and a fourth lead wire electrically connected to the second end of the resistor strip proximate the forward end of the engine component; and a measurement device electrically connected to each of the plurality of lead wires, wherein the measurement device is configured to measure a resistance of the resistor strip between each of the plurality of lead wires.

In addition to one or more of the features described above, or as an alternative, further embodiments may include that the engine component is a blade outer air seal.

In addition to one or more of the features described above, or as an alternative, further embodiments may include that the blade outer air seal includes a first surface and a second surface opposite the first surface, wherein the first surface is located radially outward from blades of the gas turbine engine, wherein the first surface is located opposite the blades, wherein the wear indication sensor attaches to the first surface.

In addition to one or more of the features described above, or as an alternative, further embodiments may include that the first surface is about concentric to a blade path of the blades.

In addition to one or more of the features described above, or as an alternative, further embodiments may include that the first end and the second end are electrically insulated from each other.

In addition to one or more of the features described above, or as an alternative, further embodiments may include that the resistor strip is located such that when the blade extends radially outward to a selected depth the resistor strip is cut into a first resistor strip and a second resistor strip, wherein the second resistor strip is electrically insulated from the first resistor strip.

In addition to one or more of the features described above, or as an alternative, further embodiments may include that the resistor strip is configured to abrade when impacted by a blade of the gas turbine engine.

According to another embodiment, a wear indication sensor is provided. The wear indication sensor comprising: a plurality of resistor strips configured to be operably attached to the surface of an engine component, each of the plurality of resistor strips including a first end and a second end; a plurality of lead wires, wherein each of the plurality of resistor strips includes one of the plurality of lead wires attached to the first end and one of the plurality of lead wires attached to second end: and a measurement device electrically connected to each of the plurality of lead wires, wherein the measurement device is configured to measure a resistance of each of the plurality of resistor strips between the first end and the second end.

In addition to one or more of the features described above, or as an alternative, further embodiments may include that the engine component is a blade outer air seal.

In addition to one or more of the features described above, or as an alternative, further embodiments may include that the blade outer air seal includes a first surface and a second surface opposite the first surface, wherein the first surface is located radially outward from blades of the gas turbine engine, wherein the first surface is located opposite the blades, wherein the wear indication sensor attaches to the first surface.

In addition to one or more of the features described above, or as an alternative, further embodiments may include that the first surface is about concentric to a blade path of the blades.

In addition to one or more of the features described above, or as an alternative, further embodiments may include that each of the plurality of resistor strips are electrically insulated from each other.

In addition to one or more of the features described above, or as an alternative, further embodiments may include that each of the plurality of resistor strips is configured to abrade when impacted by a blade of the gas turbine engine.

In addition to one or more of the features described above, or as an alternative, further embodiments may include that each of the plurality of resistor strips are intermittently space between the forward end of the engine component and the aft end of the engine component.

In addition to one or more of the features described above, or as an alternative, further embodiments may include that each of the plurality of resistor strips includes: a first resistor strip, a second resistor strip, a third resistor strip, and a fourth resistor strip.

In addition to one or more of the features described above, or as an alternative, further embodiments may include that the plurality of lead wires further comprises: a first lead wire electrically connected to the first end of the first resistor strip; a second lead wire electrically connected to the first end of the second resistor strip; a third lead wire electrically connected to the first end of the third resistor strip; a fourth lead wire electrically connected to the first end of the fourth resistor strip; a fifth lead wire electrically connected to the second end of the first resistor strip; a sixth lead wire electrically connected to the second end of the second resistor strip; a seventh lead wire electrically connected to the second end of third the resistor strip; and an eighth lead wire electrically connected to the second end of fourth the resistor strip.

According to another embodiment, a method of detecting at least one of blade clearance and blade axial shift in a gas turbine engine, the method comprising: measuring a first resistance of each of one or more resistor strips, the one or more resistor strips attached to an inner surface of a gas turbine engine opposite a blade of the gas turbine engine, wherein each of the one or more resistor strips includes a first end and a second end; operating the gas turbine engine at a first selected speed for a first period of time; measuring a second resistance of each of the one or more resistor strips after the first period of time; determining a change in resistance between the second resistance and the first resistance for each of the one or more resistor strips; and determining an amount of material removed from each of the one or more resistor strips by the blade in response to the change in resistance.

In addition to one or more of the features described above, or as an alternative, further embodiments may include that the first resistance and the second resistance of each of the one or more resistors is measured from the first end to the second end of each of the one or more resistors.

In addition to one or more of the features described above, or as an alternative, further embodiments may include that the first resistance and the second resistance of each of the one or more resistors is measured between a location on the first end proximate an aft end and a location on the first end proximate a forward end.

In addition to one or more of the features described above, or as an alternative, further embodiments may include determining at least one of an axial shift of the blade and a clearance between the blade and the inner surface in response to the amount of material removed from each of the one or more resistor strips.

The foregoing features and elements may be combined in various combinations without exclusivity, unless expressly indicated otherwise. These features and elements as well as the operation thereof will become more apparent in light of the following description and the accompanying drawings. It should be understood, however, that the following description and drawings are intended to be illustrative and explanatory in nature and non-limiting.

BRIEF DESCRIPTION

The following descriptions should not be considered limiting in any way. With reference to the accompanying drawings, like elements are numbered alike.

The detailed description explains embodiments of the present disclosure, together with advantages and features, by way of example with reference to the drawings.

DETAILED DESCRIPTION

A detailed description of one or more embodiments of the disclosed apparatus and method are presented herein by way of exemplification and not limitation with reference to the Figures.

Figure 1:
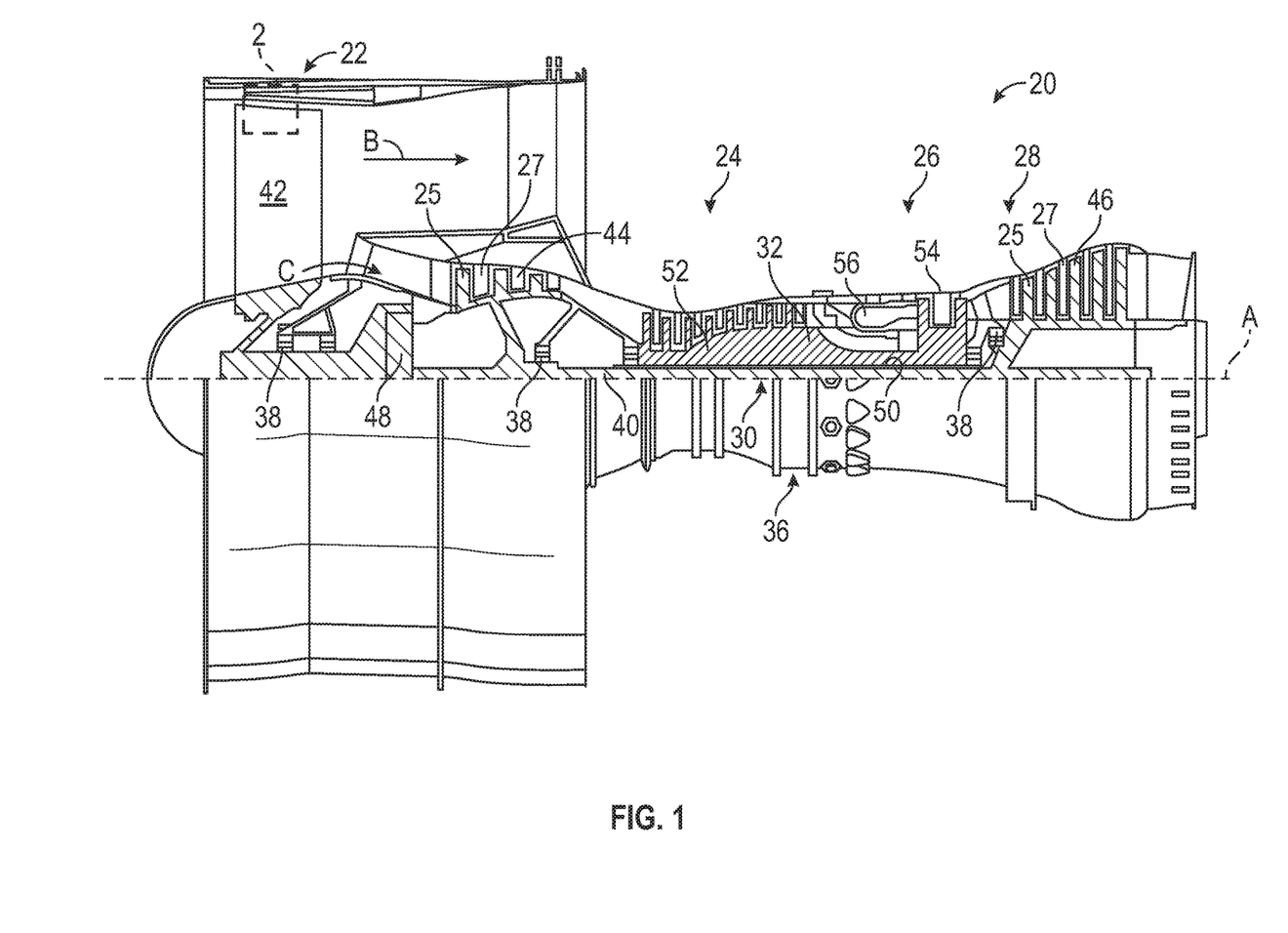
FIG. 1 is a partial cross-sectional illustration of a gas turbine engine, in accordance with an embodiment of the disclosure.

FIG. 1 schematically illustrates a gas turbine engine 20. The gas turbine engine 20 is disclosed herein as a two-spool turbofan that generally incorporates a fan section 22, a compressor section 24, a combustor section 26 and a turbine section 28. Alternative engines might include an augmentor section (not shown) among other systems or features. The fan section 22 drives air along a bypass flow path B in a bypass duct, while the compressor section 24 drives air along a core flow path C for compression and communication into the combustor section 26 then expansion through the turbine section 28. Although depicted as a two-spool turbofan gas turbine engine in the disclosed non-limiting embodiment, it should be understood that the concepts described herein are not limited to use with two-spool turbofans as the teachings may be applied to other types of turbine engines including three-spool architectures.

The exemplary engine 20 generally includes a low speed spool 30 and a high speed spool 32 mounted for rotation about an engine central longitudinal axis A relative to an engine static structure 36 via several bearing systems 38. It should be understood that various bearing systems 38 at various locations may alternatively or additionally be provided, and the location of bearing systems 38 may be varied as appropriate to the application.

The low speed spool 30 generally includes an inner shaft 40 that interconnects a fan 42, a low pressure compressor 44 and a low pressure turbine 46. The inner shaft 40 is connected to the fan 42 through a speed change mechanism, which in exemplary gas turbine engine 20 is illustrated as a geared architecture 48 to drive the fan 42 at a lower speed than the low speed spool 30. The high speed spool 32 includes an outer shaft 50 that interconnects a high pressure compressor 52 and high pressure turbine 54. A combustor 56 is arranged in exemplary gas turbine 20 between the high pressure compressor 52 and the high pressure turbine 54. An engine static structure 36 is arranged generally between the high pressure turbine 54 and the low pressure turbine 46. The engine static structure 36 further supports bearing systems 38 in the turbine section 28. The inner shaft 40 and the outer shaft 50 are concentric and rotate via bearing systems 38 about the engine central longitudinal axis A which is collinear with their longitudinal axes.

The core airflow is compressed by the low pressure compressor 44 then the high pressure compressor 52, mixed and burned with fuel in the combustor 56, then expanded over the high pressure turbine 54 and low pressure turbine 46. The turbines 46, 54 rotationally drive the respective low speed spool 30 and high speed spool 32 in response to the expansion. It will be appreciated that each of the positions of the fan section 22, compressor section 24, combustor section 26, turbine section 28, and fan drive gear system 48 may be varied. For example, gear system 48 may be located aft of combustor section 26 or even aft of turbine section 28, and fan section 22 may be positioned forward or aft of the location of gear system 48.

The engine 20 in one example is a high-bypass geared aircraft engine. In a further example, the engine 20 bypass ratio is greater than about six (6), with an example embodiment being greater than about ten (10), the geared architecture 48 is an epicyclic gear train, such as a planetary gear system or other gear system, with a gear reduction ratio of greater than about 2.3 and the low pressure turbine 46 has a pressure ratio that is greater than about five. In one disclosed embodiment, the engine 20 bypass ratio is greater than about ten (10:1), the fan diameter is significantly larger than that of the low pressure compressor 44, and the low pressure turbine 46 has a pressure ratio that is greater than about five 5:1. Low pressure turbine 46 pressure ratio is pressure measured prior to inlet of low pressure turbine 46 as related to the pressure at the outlet of the low pressure turbine 46 prior to an exhaust nozzle. The geared architecture 48 may be an epicycle gear train, such as a planetary gear system or other gear system, with a gear reduction ratio of greater than about 2.3:1. It should be understood, however, that the above parameters are only exemplary of one embodiment of a geared architecture engine and that the present disclosure is applicable to other gas turbine engines including direct drive turbofans.

A significant amount of thrust is provided by the bypass flow B due to the high bypass ratio. The fan section 22 of the engine 20 is designed for a particular flight condition—typically cruise at about 0.8 Mach and about 35,000 feet (10,688 meters). The flight condition of 0.8 Mach and 35,000 ft (10,688 meters), with the engine at its best fuel consumption—also known as "bucket cruise Thrust Specific Fuel Consumption ('0')"—is the industry standard parameter of lbm of fuel being burned divided by lbf of thrust the engine produces at that minimum point. "Low fan pressure ratio" is the pressure ratio across the fan blade alone, without a Fan Exit Guide Vane ("FEGV") system. The low fan pressure ratio as disclosed herein according to one non-limiting embodiment is less than about 1.45. "Low corrected fan tip speed" is the actual fan tip speed in ft/sec divided by an industry standard temperature correction of [(Tram ° R)/(518.7° R)]0.5. The "Low corrected fan tip speed" as disclosed herein according to one non-limiting embodiment is less than about 1150 ft/second (350.5 m/sec).

Figure 2:
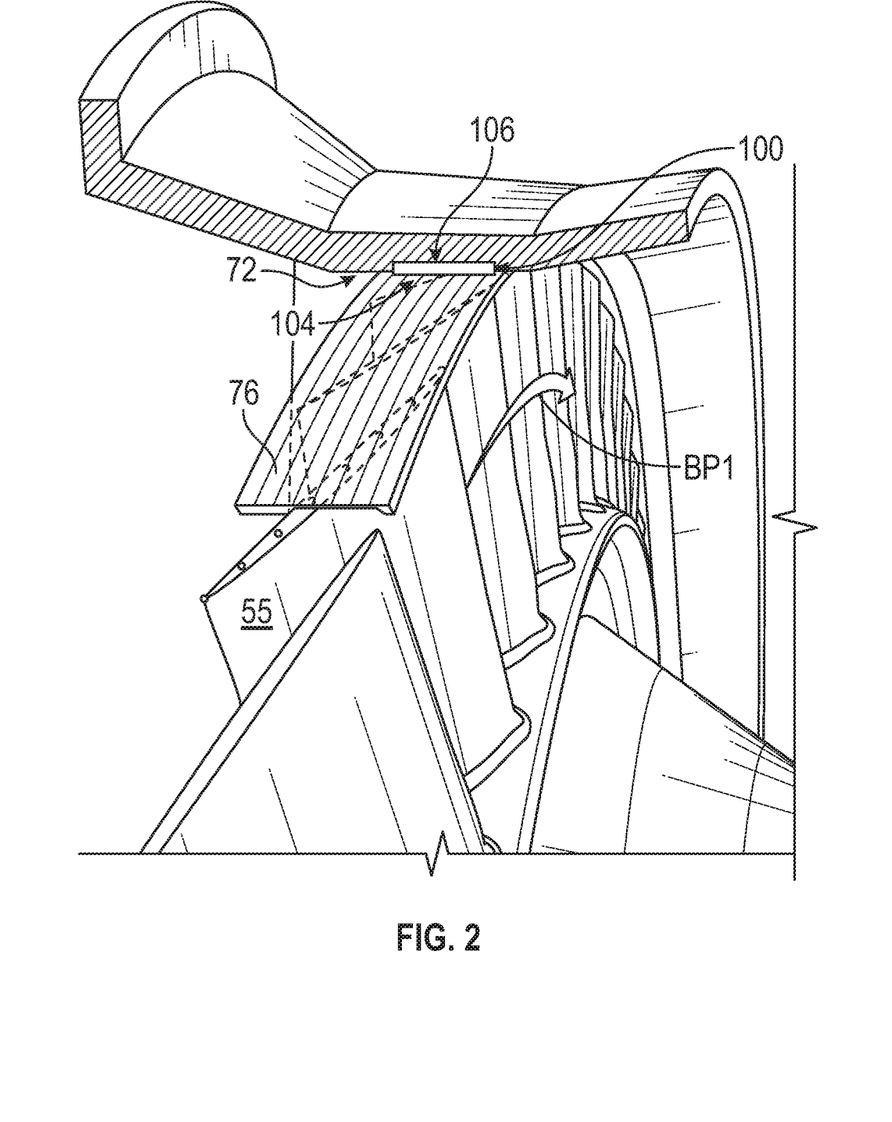
FIG. 2 is a cross-sectional illustration of a wear indication sensor attached to an inner surface of a gas turbine engine, in accordance with an embodiment of the disclosure.

Referring now to FIG. 2, which shows a cross-sectional view of a rub depth and axial shift indication sensor that will be referred to as a wear indication sensor 100 installed in a gas turbine engine 20, in accordance with an embodiment of the disclosure. The wear indication sensor 100 is configured to measure wear depth of a blade 55 and/or axial shift of the blade 55. One or more wear indication sensors 100 may be affixed to or embedded in the inner surface 72 of the gas turbine engine 20 in order to monitor the clearance between the blade 55 and the inner surface 72. As seen in FIG. 2, the wear indication sensor 100 is attached to and/or embedded in an inner surface 72 of the gas turbine engine 20 opposite a blade 55 of the gas turbine engine 20. In the illustrated embodiment, the wear indication sensor 100 is attached to or embedded in a blade outer air seal 76, which is the inner surface 72 in the illustrated embodiment. The blade outer air seal 76 includes a first surface 104 and a second surface 106 opposite the first surface. As shown FIG. 2, the first surface 104 is located radially outward from the blades 55 and opposite the blades 55. The first surface 104 is about concentric to a blade path BP1 of the blades 55. The second surface 106 is located radially outward from the first surface 104. In the embodiment illustrated in FIG. 2, the wear indication sensor 100 has been installed proximate the fan 42 of the gas turbine engine 20 but it is understood that the wear indication sensor 100 may be located in other locations including but not limited to the compressor section 24 and/or the turbine section 28 (see FIG. 1).

Referring now to FIGS. 3a, 3b, 3c, and 3d with continued reference to FIGS. 1-2. FIGS. 3a-3d each show a first configuration 100a of a wear indication sensor 100 installed in a gas turbine engine 20, in accordance with an embodiment of the disclosure. The wear indication sensor 100 is attached to an inner surface 72 of the gas turbine engine 20 opposite a blade 55 of the gas turbine engine 20. The blade 55 rotates along the blade path BP1. In the illustrated embodiment, the wear indication sensor 100 is attached to a blade outer air seal 76, thus the blade outer air seal 76 is the inner surface 72. One or more wear indication sensors 100 may be affixed to the inner surface 72 of the gas turbine engine 20 in order to monitor the clearance between the blade 55 and the inner surface 72, a method discussed further below in FIG. 5.

As shown in FIGS. 3a-3d, the first configurations 100a of the wear indication sensor 100 include a plurality of lead wires 120. The plurality of lead wires may include a first lead wire 120a, a second lead wire 120b, a third lead wire 120c, and a fourth lead wire 120d. Each lead wire 120a-120d may be enclosed in insulation 130, as seen in FIGS. 3a-3d.

Figure 3A:
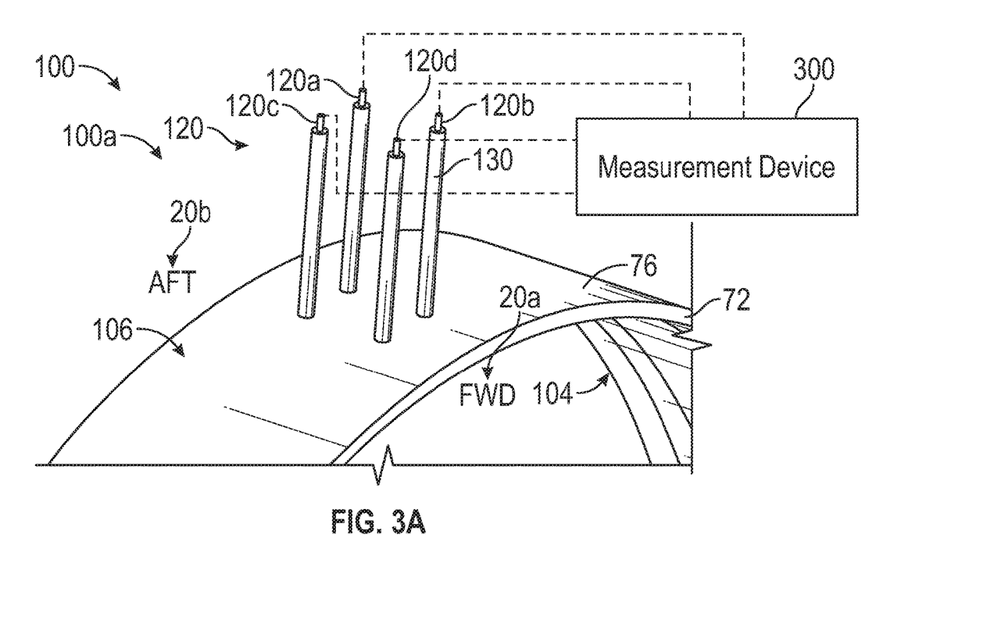
FIG. 3a-3d are illustrations of a first configuration of a wear indication sensor, in accordance with an embodiment of the disclosure.
Figure 3B:
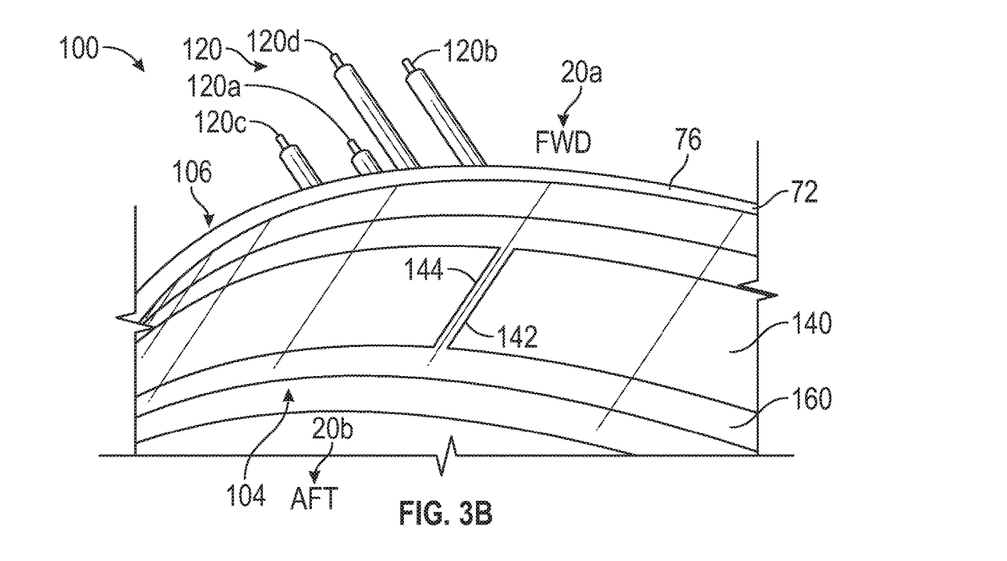
Figure 3C:
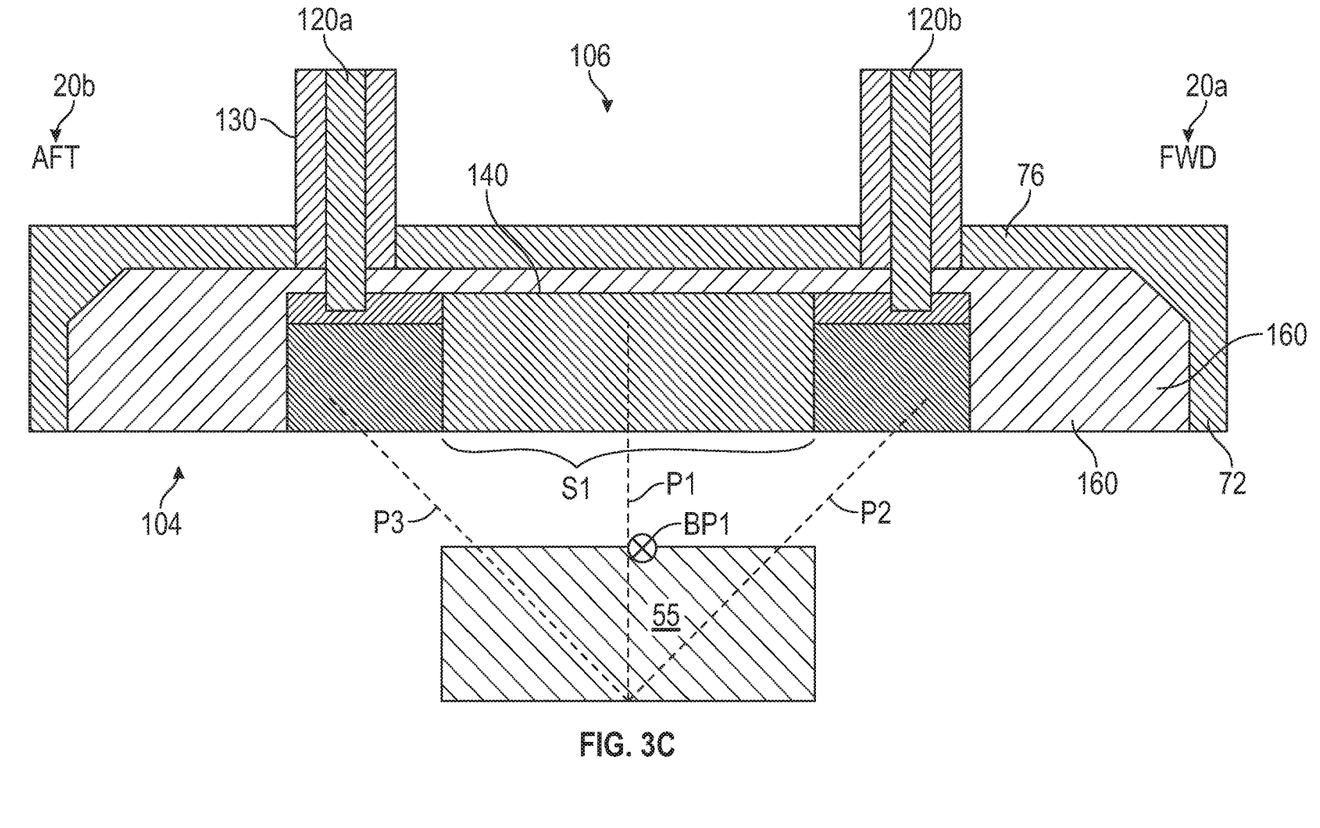

As seen in FIGS. 3b and 3c, a resistor strip 140 is located on the first surface 104 of the blade outer air seal 76. The resistor strip 140 may be composed of electrically resistive and abradable material, such as, for example FeCrAl. The resistor strip 140 is designed to abrade when struck by the blade 55. The resistive strip 140 may be operably attached the inner surface 72 by an adhesive and/or printed directly on the inner surface 72 through a direct writing manufacturing process, such as, for example, additive manufacturing, 3D printing, extrusion dispensing, micro dispensing, ink jet, thermal spray, plasma spray, laser ablation, or similar process known to one of skill in the art. The resistor strip 140 includes a first end 142 and a second end 144. The first end 142 and the second end 144 are electrically separated by an insulating abradable coating 160. The insulating abradable coating 160 is designed abrade when struck by the blade 55.

Each of the plurality of wires 120 may extend into the blade outer air seal 76 from the second surface 106 and electrically connect to the resistor strip 140. The first lead wire 120a and the second lead wire 120b may be electrically connected to the first end 142 of the resistor strip 140. The first lead wire 120a may be electrically connected to the first end 142 proximate an aft end 20b and the second lead wire 120b may be electrically connected to the first end 142 proximate a forward end 20a. The third lead wire 120c and the fourth lead wire 120d may be electrically connected to the second end 144 of the resistor strip 140. The third lead wire 120c may be electrically connected to the second end 144 proximate an aft end 20b and the fourth lead wire 120d may be electrically connected to the second end 144 proximate a forward end 20a.

Each of the plurality of lead wires 120 may be electrically connected to a measurement device 300 configured to measure the resistance through resistor strip 140, as seen in FIG. 3a. The resistance may be measured from the first end 142 to the second end 144 (ex: between the first lead wire 120a and the third lead wire 120c; between the second lead wire 120b and the fourth lead wire 120d). The resistance may also be measured from the first end 142 to the second end 144 between a location on the first end 142 proximate the aft end 22*b* and a location on the first end 142 proximate the forward end 22*a* (ex: between the first wire 120*a* and the second wire 120*b*; between the third wire 120*c* and the fourth wire 120*d*). The measurement device 300 may include a processor and a memory. For ease of illustration, the processor and memory are not shown in FIG. 3*a*. The processor can be any type or combination of computer processors, such as a microprocessor, microcontroller, digital signal processor, application specific integrated circuit, programmable logic device, and/or field programmable gate array. The memory is an example of a non-transitory computer readable storage medium tangibly embodied in or operably connected to the path determination system including executable instructions stored therein, for instance, as firmware.

The resistor strip 140 has a known resistance, thus the resistance between each of the plurality of lead wires 120 is known. Advantageously, since the resistor strip 140 has a known resistance, as the blade 55 cuts into the wear indication sensor 100 removing a portion of the resistor strip 140 then the depth that the blade 55 cut into the wear indication sensor 100 may be determined by measuring the resistance after the cut and comparing to the original resistance prior to the cut. As may be seen in FIGS. 3*c* and 3*d*, the blade 55 may extend into the resistor strip 140 as the blade rotates though the blade path BP1 and remove portions of the resistor strip 140. The blade may extend radially outward along a first path P1 and begin to remove a first section Si of the resistor strip 140. If the entire first section Si of the resistor strip 140 is removed then the resistor strip 140 will be split into a first resistor strip 140*a* and a second resistor strip 140*b*. A change in resistance between the first lead wire 120*a* and the second lead wire 120*b* may be detected when the first section Si of the resistor strip 140 is removed and the resistor strip 140 is split into a first resistor strip 140*a* and a second resistor strip 140*b*. Similarly, a change in resistance between the third lead wire 120*c* and the fourth lead wire 120*d* may be detected when the first section Si of the resistor strip 140 is removed and the resistor strip 140 is split into a first resistor strip 140*a* and a second resistor strip 140*b*.

Figure 3D:
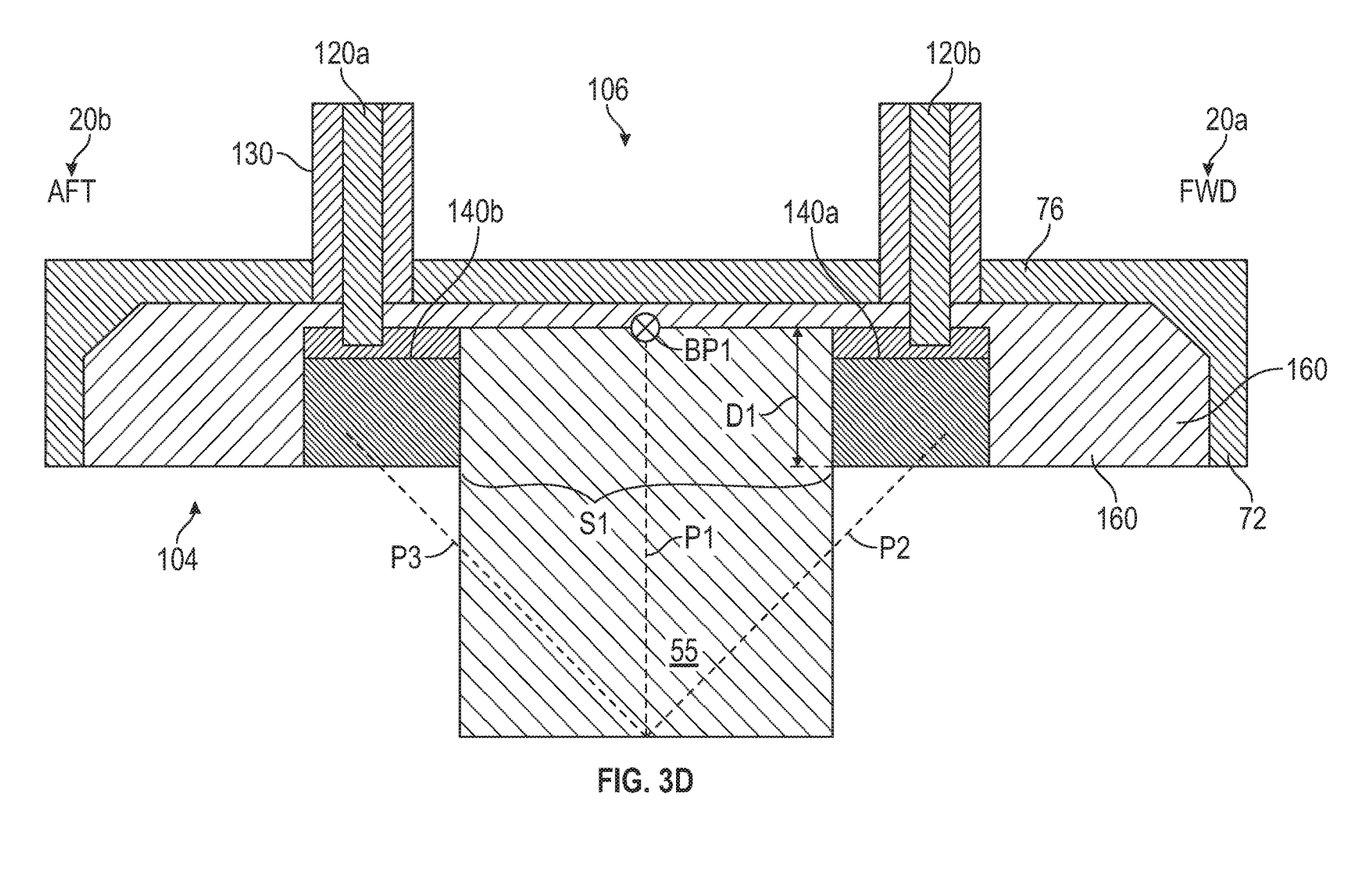

A change in resistance indicating that the resistor strip 140 has been split into two would also indicate that the blade 55 has penetrated a selected depth D1 into the wear indication sensor 100. If the blade 55 begins to shift towards the forward end 20*a* near a second path P2 then a portion of the first resistor strip 140*a* may be removed and a change of resistance would be detected between the second lead wire 120*b* and the fourth lead wire 120*d*. If the blade 55 begins to shift towards the aft end 20*b* near the third path P3 then a portion of the first resistor strip 140*a* may be removed and a change of resistance would be detected between the first lead wire 120*a* and the third lead wire 120*c*.

Figure 4A:
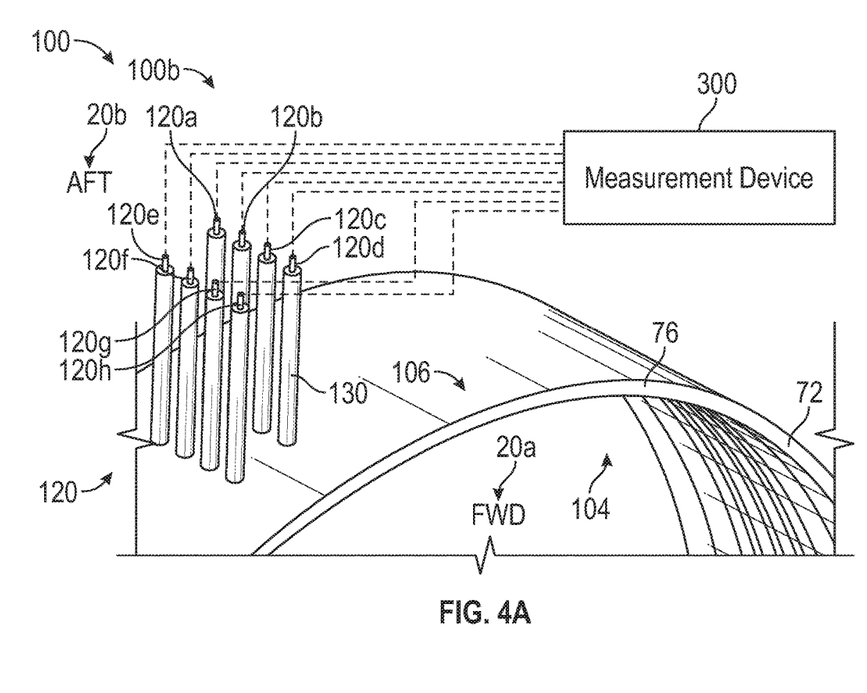
FIG. 4a-4c are illustrations of a second configuration of a wear indication sensor, in accordance with an embodiment of the disclosure.
Figure 4B:
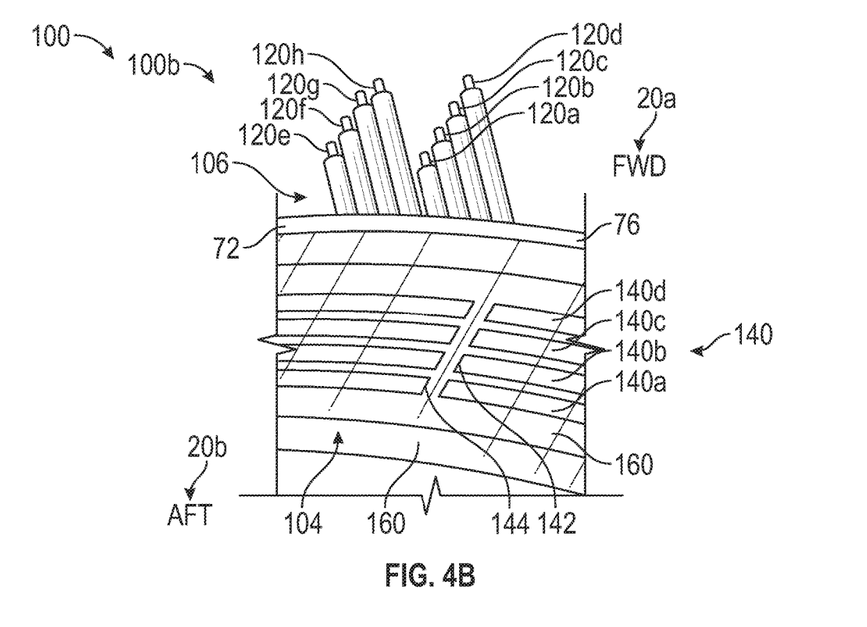
Figure 4C:
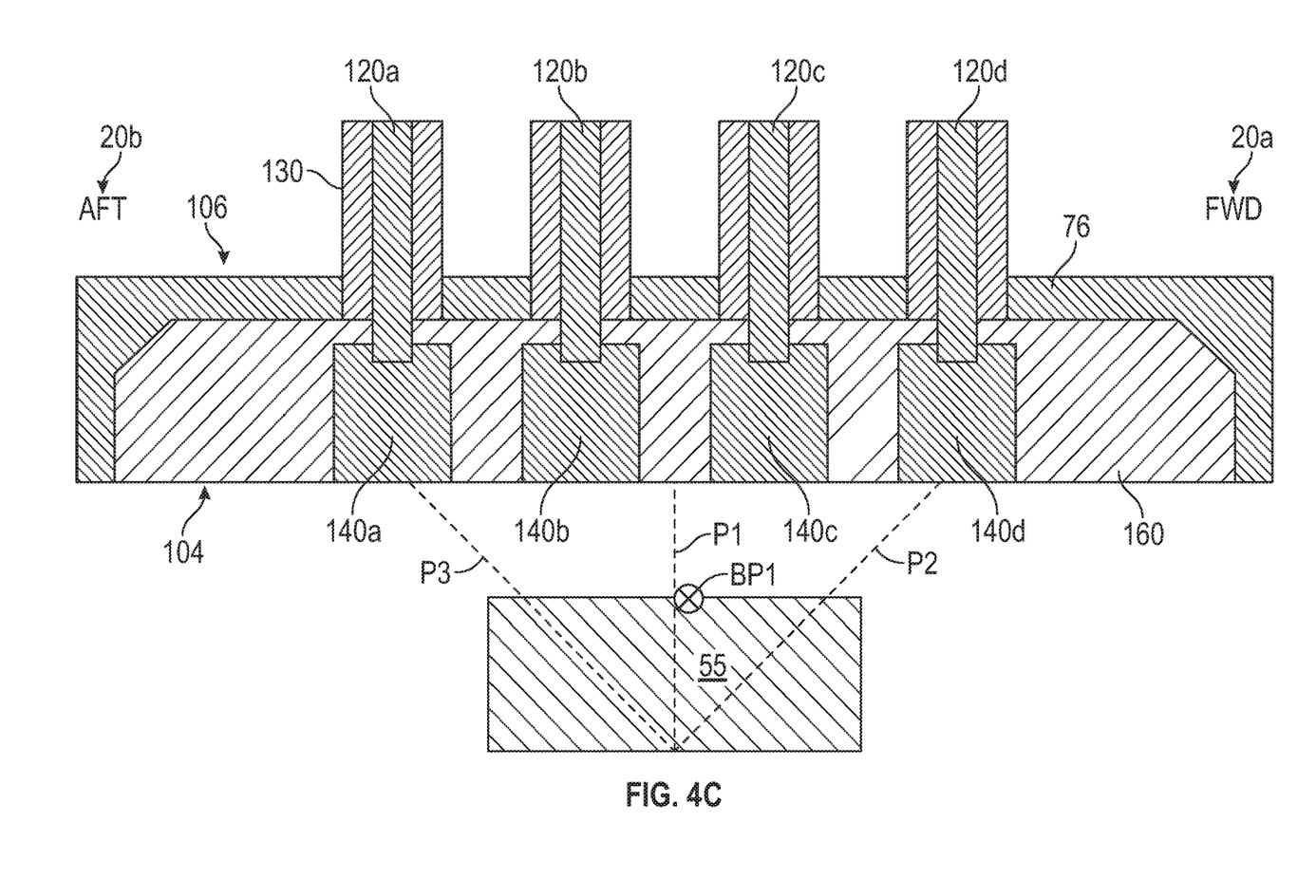

Referring now to FIGS. 4*a*, 4*b*, and 4*c* with continued reference to FIGS. 1-2. FIGS. 4*a*-4*c* each show a second configuration 100*b* of a wear indication sensor 100 installed in a gas turbine engine 20, in accordance with an embodiment of the disclosure. The wear indication sensor 100 is attached to an inner surface 72 of the gas turbine engine 20 opposite a blade 55 of the gas turbine engine 20. The blade 55 rotates along the blade path BP1. In the illustrated embodiment, the wear indication sensor 100 is attached to a blade outer air seal 76, thus the blade outer air seal 76 is the inner surface 72. One or more wear indication sensors 100 may be affixed to the inner surface 72 of the gas turbine engine 20 in order to monitor the clearance between the blade 55 and the inner surface 72, a method discussed further below in FIG. 5.

As shown in FIGS. 4*a*-4*c*, the second configuration 100*b* of the wear indication sensor 100 include a plurality of lead wires 120. The plurality of lead wires may include a first lead wire 120*a*, a second lead wire 120*b*, a third lead wire 120*c*, a fourth lead wire 120*d*, a fifth lead wire 120*e*, a sixth lead wire 120*f*, a seventh lead wire 120*g*, and an eighth lead wire 120*h*. Each lead wire 120*a*-120*h* may be enclosed in insulation 130, as seen in FIGS. 4*a*-4*d*.

As seen in FIGS. 4*b* and 4*c*, a plurality of resistor strips 140 are located on the first surface 104 of the blade outer air seal 76. The plurality of resistor strips 140 may include a first resistor strip 140*a*, a second resistor strip 140*b*, a third resistor strip 140*c*, and a fourth resistor strip 140*d*. The plurality of resistor strips 140 may each composed of electrically resistive and abradable material, such as, for example FeCrAl. Each of the plurality of resistor strips 140*a*-140*d* is designed to abrade when struck by the blade 55. Each of the plurality of resistor strips 140 may be operably attached the inner surface 72 by an adhesive and/or printed directly on the inner surface 72 through a direct writing manufacturing process, such as, for example, additive manufacturing, 3D printing, extrusion dispensing, micro dispensing, ink jet, thermal spray, laser ablation, or similar process known to one of skill in the art. Each of the plurality of resistor strips 140 begins at a first end 142 and ends at a second end 144. The first end 142 and the second end 144 are electrically separated by an insulating abradable coating 160. The insulating abradable coating 160 is designed abrade when struck by the blade 55. Further each of the plurality of resistor strips 140 may be electrically separated from each other by the insulating abradable coating 160, as seen in FIG. 4*b*.

Each of the plurality of wires 120 may extend into the blade outer air seal 76 from the second surface 106 and electrically connect to each of the plurality of resistor strips 140. The first lead wire 120*a* may be electrically connected to the first end 142 of the first resistor strip 140*a* and the fifth lead wire 120*e* may be electrically connected to the second end 144 of the first resistor strip 140*a*, as seen in FIG. 4*b*. The second lead wire 120*b* may be electrically connected to the first end 142 of the second resistor strip 140*b* and the sixth lead wire 120*f* may be electrically connected to the second end 144 of the second resistor strip 140*b*, as seen in FIG. 4*b*. The third lead wire 120*c* may be electrically connected to the first end 142 of the third resistor strip 140*c* and the seventh lead wire 120*g* may be electrically connected to the second end 144 of the third resistor strip 140*c*, as seen in FIG. 4*b*. The fourth lead wire 120*d* may be electrically connected to the first end 142 of the fourth resistor strip 140*d* and the eighth lead wire 120*h* may be electrically connected to the second end 144 of the fourth resistor strip 140*d*, as seen in FIG. 4*b*.

Each of the plurality of lead wires 120 may be electrically connected to a measurement device 300 configured to measure the resistance through each resistor strip 140, as seen in FIG. 4*a*. The resistance may be measured from the first end 142 to the second end 144 (ex: between the first lead wire 120*a* and the fifth lead wire 120*e*; between the second lead wire 120*b* and the sixth lead wire 120*f*; between the third lead wire 120*c* and the seventh lead wire 120*g*; between the fourth lead wire 120 and the eighth lead wire 120*h*). The measurement device 300 may include a processor and a memory. For ease of illustration, the processor and memory are not shown in FIG. 4*a*. The processor can be any type or combination of computer processors, such as a microprocessor, microcontroller, digital signal processor, application specific integrated circuit, programmable logic device, and/or field programmable gate array. The memory is an example of a non-transitory computer readable storage medium tangibly embodied in or operably connected to the path determination system including executable instructions stored therein, for instance, as firmware.

Each of the plurality of resistor strips 140 has a known resistance, thus the resistance between each of the plurality of lead wires 120 is known. Advantageously, since each of the plurality of resistor strips 140 has a known resistance, as the blade 55 cuts into the wear indication sensor 100 removing a portion of the resistor strip 140 then the depth that the blade 55 cut into the wear indication sensor 100 may be determined by measuring the resistance after the cut and comparing to the original resistance prior to the cut. Further each of the plurality of resistor strips 140 is intermittently spaced along the first surface 104 from the forward end 20b to the aft end 20b, thus axial shift of the blade 55 may be determined by determining which of the plurality of resistor strips 140 is experiencing a change in resistance.

As may be seen in FIG. 4c, the blade 55 may rotate along BP1 and may extend into one or more resistor strips 140 and remove portions of one resistor strip 140. The blade may extend radially outward along a first path P1 and begin to remove portions of the second resistor strip 140b or the third resistor strip 140c. If the blade 55 begins to shift towards the forward end 20a near the second path P2, then a greater portion of the third resistor strip 140c may be removed than the second resistor strip 140b, thus resulting in a higher resistance for the second resistor strip 140b in comparison to the third resistor strip 140c. Additionally, if the blade 55 begins to shift towards the forward end 20a near the second path P2, then a portion of the fourth resistor strip 140d may be removed, thus resulting in a decreased resistance of the fourth resistor strip 140d. If the blade 55 begins to shift towards the aft end 20b near the third path P3, then a greater portion of the second resistor strip 140b may be removed than the third resistor strip 140c, thus resulting in a higher resistance for the third resistor strip 140c in comparison to the second resistor strip 140b. Additionally, if the blade 55 begins to shift towards the aft end 20b near the third path P3, then a portion of the first resistor strip 140a may be removed, thus resulting in a decreased resistance of the first resistor strip 140a.

It is understood that the example of four resistor strips 140 illustrated in FIGS. 4a-4c are for illustrative purposes and any number of resistor strips 140 may be used and spaced intermittently along the first surface 104 from the forward end 20b to the aft end 20b. Advantageously, increasing the number of intermittently spaced resistors strips also increases fidelity of measuring axial shift of the blade 55.

Figure 5:
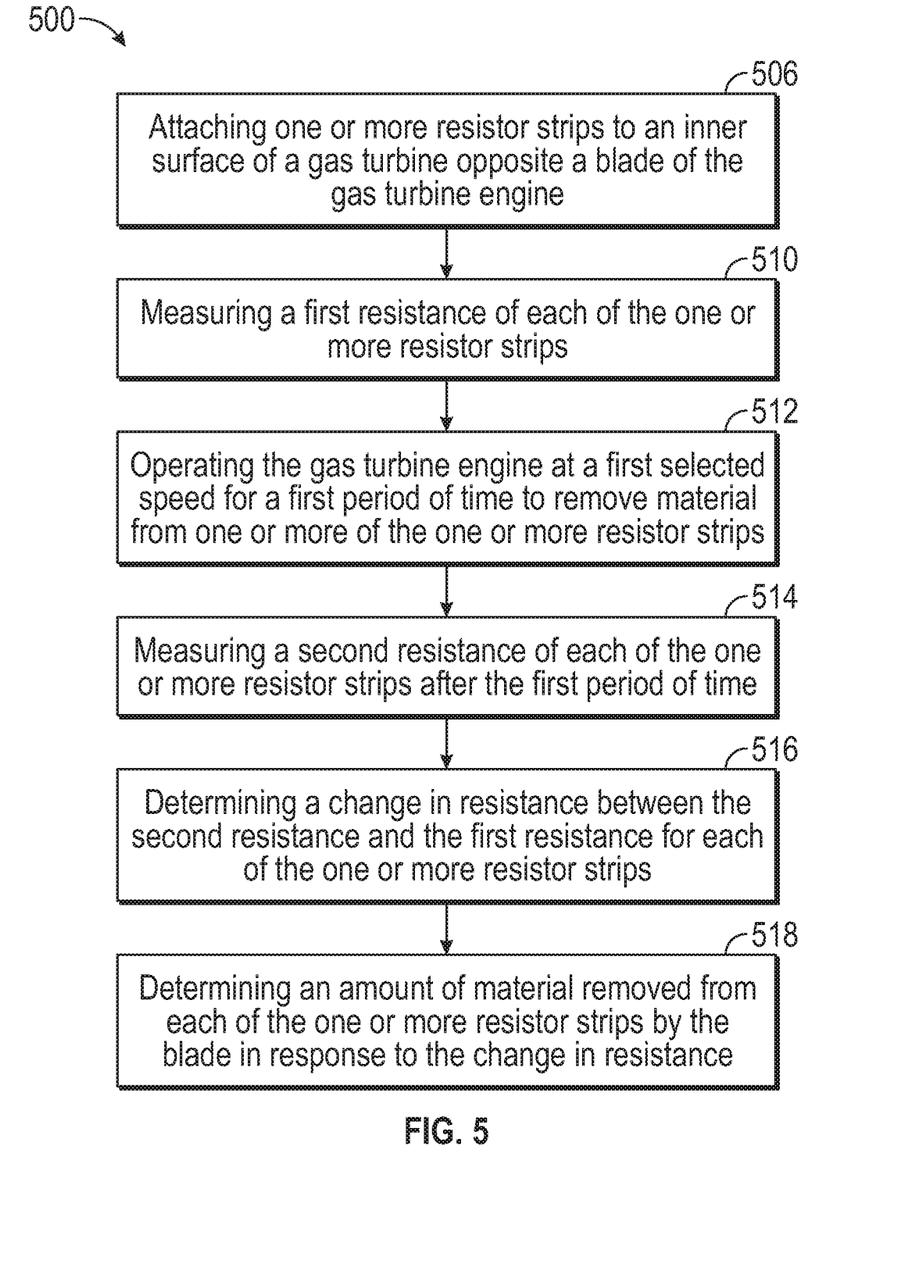
FIG. 5 is a flow chart illustrating a method of detecting at least one of blade clearance and blade axial shift within a gas turbine engine, in accordance with an embodiment of the disclosure.

Referring now to FIG. 5 with continued reference to FIGS. 1-4. FIG. 5 is a flow chart illustrating a method 500 for detecting at least one of blade clearance and axial blade shift in a gas turbine engine 20, in accordance with an embodiment. At block 506, the one or more resistor strips 140 are attached to an inner surface 72 of a gas turbine engine 20 opposite a blade 55 of the gas turbine engine 20. As discussed above, the wear indication sensors 100 may be composed of one or more resistor strips 140. In first configuration 100a, the wear indication sensor 100 is composed of one wear indication strip 140 that split in to two wear indications strips 140a, 140b after the blade reached a selected depth D1. In the second configuration 100b, the wear indication sensor 100 is composed of a plurality of resistor strips 140 intermittently spaced from a forward end 20a to an aft end 20b. At block 510, a first resistance of each of the one or more resistor strips 140 is measured. At block 512, the gas turbine engine 20 is operated at a first selected speed for a first period of time to remove material from one or more of the one or more resistor strips 140. At block 514, a second resistance of each of the one or more resistor strips is measured after the first period of time. The first resistance and second resistance of each of the one or more resistors 140 may be measured from the first end 142 to the second end 144 of each of the one or more resistors 140. The first resistance and second resistance of each of the one or more resistors 140 may be measured between a location on the first end 142 proximate an aft end 22b and a location on the first end 142 proximate a forward end 22a, as was seen as a capability in the first configuration 100a of the wear indication sensor 100 in FIGS. 3a-3d.

The second resistance of each of the one or more resistors 140 may be measured by shutting down the engine 20 after each engine speed of interest is performed on the engine 20, letting the engine 20 cool and then taking the resistance measurement. The engine speeds tested (first engine speed, second engine speed . . . etc.) may represent different flight conditions experienced by the engine 20 including but not limited to ground idle, flight idle, max cruise, take-off, max power, and any other flight condition known to one of skill in the art. The second resistance of each of the one or more resistors 140 may also be measured without shutting down the engine 20; however the temperature of each resistor 140 would have to be measured and an appropriate correction factor for the material of each resistor 140 at the temperature measured would have to be factored in to calculate the correct second resistance. Alternatively, the temperature may not have to be measured by utilizing a control resistor strip (not shown) that is located near the resistor strips 140. The control resistor strip would be in a location such that it never gets abraded but sees the same temperature loads as the resistors strips 140. Thus, the resistance of resistor strips 140 may be compared to the resistance of the control resistor strip to factor out any temperature change and calculate the correct second resistance.

At block 516, a change in resistance between the second resistance and the first resistance is determined for each of the one or more resistor strips 140. At block 518, an amount of material removed from each of the one or more resistor strips 140 by the blade 55 is determined in response to the change in resistance. Method 500 may also include: determining a clearance between the blade 55 and the inner surface 72 in response to the amount of material removed from each of the one or more resistor strips 140. Method 500 may further include: determining an axial shift of the blade 55 in response to the amount of material removed from each of the one or more resistor strips 140.

While the above description has described the flow process of FIG. 5 in a particular order, it should be appreciated that unless otherwise specifically required in the attached claims that the ordering of the steps may be varied.

Technical effects of embodiments of the present disclosure include using a one or more resistor strips to determine blade tip clearance through detecting a change in electrical resistance.

The term "about" is intended to include the degree of error associated with measurement of the particular quantity based upon the equipment available at the time of filing the application. For example, "about" can include a range of ±8% or 5%, or 2% of a given value.

The terminology used herein is for the purpose of describing particular embodiments only and is not intended to be limiting of the present disclosure. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, element components, and/or groups thereof.

While the present disclosure has been described with reference to an exemplary embodiment or embodiments, it will be understood by those skilled in the art that various changes may be made and equivalents may be substituted for elements thereof without departing from the scope of the present disclosure. In addition, many modifications may be made to adapt a particular situation or material to the teachings of the present disclosure without departing from the essential scope thereof. Therefore, it is intended that the present disclosure not be limited to the particular embodiment disclosed as the best mode contemplated for carrying out this present disclosure, but that the present disclosure will include all embodiments falling within the scope of the claims.

What is claimed is:

1. A wear indication sensor, the wear indication sensor comprising:
   a resistor strip configured to be operably attached to the surface of an engine component, the resistor strip including a first end and a second end;
   a plurality of lead wires comprising:
      a first lead wire electrically connected to the first end of the resistor strip proximate an aft end of the resistor strip;
      a second lead wire electrically connected to the first end of the resistor strip proximate a forward end of the resistor strip;
      a third lead wire electrically connected to the second end of the resistor strip proximate the aft end of the resistor strip; and
      a fourth lead wire electrically connected to the second end of the resistor strip proximate the forward end of the resistor strip; and
   a measurement device electrically connected to each of the plurality of lead wires, wherein the measurement device is configured to measure a resistance of the resistor strip between each of the plurality of lead wires.

2. The wear indication sensor of claim 1, wherein the engine component is a blade outer air seal.

3. The wear indication sensor of claim 2, wherein the blade outer air seal includes a first surface and a second surface opposite the first surface, wherein the first surface is located radially outward from blades of the gas turbine engine, wherein the first surface is located opposite the blades, wherein the wear indication sensor attaches to the first surface.

4. The wear indication sensor of claim 3, wherein the first surface is about concentric to a blade path of the blades.

5. The wear indication sensor of claim 1, wherein the first end and the second end are electrically insulated from each other.

6. The wear indication sensor of claim 1, wherein the resistor strip is located such that when the blade extends radially outward to a selected depth the resistor strip is cut into a first resistor strip and a second resistor strip, wherein the second resistor strip is electrically insulated from the first resistor strip.

7. The wear indication sensor of claim 1, wherein the resistor strip is configured to abrade when impacted by a blade of the gas turbine engine.

8. An engine component of a gas turbine engine, comprising:
   a surface;
   a wear indication sensor comprising:
      a plurality of resistor strips operably attached to the surface, each of the plurality of resistor strips including a first end and a second end, wherein the plurality of resistor strips are staggered intermittently between a forward end of the engine component and an aft end of the engine component;
      a plurality of lead wires, wherein each of the plurality of resistor strips includes one of the plurality of lead wires attached to the first end and one of the plurality of lead wires attached to the second end: and
      a measurement device electrically connected to each of the plurality of lead wires, wherein the measurement device is configured to measure a resistance of each of the plurality of resistor strips between the first end and the second end.

9. The engine component of claim 8, wherein the engine component is a blade outer air seal.

10. The engine component of claim 9, wherein the blade outer air seal includes a first surface and a second surface opposite the first surface, wherein the first surface is located radially outward from blades of the gas turbine engine, wherein the first surface is located opposite the blades, wherein the wear indication sensor attaches to the first surface.

11. The engine component of claim 10, wherein the first surface is about concentric to a blade path of the blades.

12. The engine component of claim 8, wherein each of the plurality of resistor strips are electrically insulated from each other.

13. The engine component of claim 8, wherein each of the plurality of resistor strips is configured to abrade when impacted by a blade of the gas turbine engine.

14. The engine component of claim 8, wherein each of the plurality of resistor strips includes: a first resistor strip located proximate the aft end, a second resistor strip, a third resistor strip, and a fourth resistor strip located proximate the forward end, wherein the fourth resistor strip is located forward of the third resistor strip, the third resistor strip is located forward of the second resistor strip, and the second resistor strip is located forward of the first resistor strip.

15. The engine component of claim 14, wherein the plurality of lead wires further comprises:
   a first lead wire electrically connected to the first end of the first resistor strip;
   a second lead wire electrically connected to the first end of the second resistor strip;
   a third lead wire electrically connected to the first end of the third resistor strip;
   a fourth lead wire electrically connected to the first end of the fourth resistor strip;
   a fifth lead wire electrically connected to the second end of the first resistor strip;
   a sixth lead wire electrically connected to the second end of the second resistor strip;
   a seventh lead wire electrically connected to the second end of third the resistor strip; and an eighth lead wire electrically connected to the second end of fourth the resistor strip.

16. A method of detecting at least one of blade clearance and blade axial shift in a gas turbine engine, the method comprising:
- measuring a first resistance of each of one or more resistor strips, the one or more resistor strips attached to an inner surface of a gas turbine engine component opposite a blade of the gas turbine engine, wherein each of the one or more resistor strips includes a first end and a second end, and wherein the one or more resistor strips are staggered intermittently between a forward end of the gas turbine engine component and an aft end of the gas turbine engine component;
- operating the gas turbine engine at a first selected speed for a first period of time;
- measuring a second resistance of each of the one or more resistor strips after the first period of time;
- determining a change in resistance between the second resistance and the first resistance for each of the one or more resistor strips; and
- determining an amount of material removed from each of the one or more resistor strips by the blade in response to the change in resistance.

17. The method of claim 16, wherein:
the first resistance and the second resistance of each of the one or more resistor strips is measured from the first end to the second end of each of the one or more resistor strips.

18. The method of claim 16, wherein:
the first resistance and the second resistance of each of the one or more resistor strips is measured between a location on the first end proximate an aft end and a location on the first end proximate a forward end.

19. The method of claim 16, further comprises:
determining at least one of an axial shift of the blade and a clearance between the blade and the inner surface in response to the amount of material removed from each of the one or more resistor strips.

\* \* \* \* \*